United States Patent
Molema et al.

(10) Patent No.: US 8,678,051 B2
(45) Date of Patent: *Mar. 25, 2014

(54) INSTRUMENT, A SYSTEM AND A CONTAINER FOR PROVISIONING A DEVICE FOR PERSONAL CARE TREATMENT, AND A DEVICE FOR PERSONAL CARE TREATMENT WITH SUCH A CONTAINER

(75) Inventors: Jeroen Molema, Drachten (NL); Wilko Westerhof, Drachten (NL); Bartele Hendrik De Vries, Drachten (NL); Reinier Niels Lap, Surhuizum (NL); Olaf Martin De Jong, Drachten (NL); Bart-Jan Zwart, Foxhol (NL); Johannes Rogier De Vrind, Groningen (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/606,593

(22) Filed: Sep. 7, 2012

(65) Prior Publication Data
US 2013/0008562 A1 Jan. 10, 2013

Related U.S. Application Data

(63) Continuation of application No. 12/293,312, filed on Sep. 17, 2008, now Pat. No. 8,281,824.

(30) Foreign Application Priority Data

Mar. 24, 2006 (EP) .................................... 06111711

(51) Int. Cl.
*B65B 1/04* (2006.01)
*B60K 15/04* (2006.01)

(52) U.S. Cl.
CPC ..................................... *B60K 15/04* (2013.01)
USPC ........... 141/350; 141/346; 141/347; 141/348; 141/349; 137/614.04

(58) Field of Classification Search
USPC ....................... 141/346–352, 357; 137/614.04
See application file for complete search history.

(56) References Cited

U.S. PATENT DOCUMENTS

| | | |
|---|---|---|
| 3,422,864 A | 1/1969 | Allinquant |
| 5,758,700 A | 6/1998 | Vanderploeg |
| 6,039,301 A | 3/2000 | Westerhof |

(Continued)

FOREIGN PATENT DOCUMENTS

| | | |
|---|---|---|
| DE | 1247900 B | 8/1967 |
| DE | 19801111 A1 | 7/1999 |

(Continued)

*Primary Examiner* — Timothy L Maust

(57) ABSTRACT

An instrument for filling a substance supply container of a device for personal care treatment has a filling needle having a proximal end connected or connectable to a storage reservoir and a distal end, a substance transport conduit extending from the proximal end to at least one outlet provided in a radially facing surface portion closely adjacent the distal end of the filling needle. A sleeve is arranged around the filling needle and is movable between a first position closing off the at least one outlet and a second position proximally away from the first position and the at least one outlet. A system including such an instrument, a container for cooperation with such an instrument and for provisioning a device for personal care treatment as well as a device for personal care treatment including such a container are described.

15 Claims, 4 Drawing Sheets

(56) References Cited

U.S. PATENT DOCUMENTS

| | | | |
|---|---|---|---|
| 6,220,772 | B1 | 4/2001 | Taylor |
| 7,264,026 | B2 | 9/2007 | Gruber |
| 7,703,486 | B2 | 4/2010 | Costanzo |
| 8,281,824 | B2 * | 10/2012 | Molema et al. ............... 141/350 |
| 2004/0062591 | A1 | 4/2004 | Hall |
| 2005/0004498 | A1 | 1/2005 | Klupt |
| 2010/0252143 | A1 | 10/2010 | Juo |

FOREIGN PATENT DOCUMENTS

| | | |
|---|---|---|
| EP | 0702913 A2 | 3/1996 |
| FR | 2382319 A1 | 9/1978 |
| GB | 2399005 A | 9/2004 |
| WO | 0076905 A2 | 12/2000 |

* cited by examiner

INSTRUMENT, A SYSTEM AND A CONTAINER FOR PROVISIONING A DEVICE FOR PERSONAL CARE TREATMENT, AND A DEVICE FOR PERSONAL CARE TREATMENT WITH SUCH A CONTAINER

The invention relates to an instrument for filling a substance supply container of a device for personal care treatment, comprising a filling needle having a distal end, a proximal end suitable for connection to a storage reservoir, and a substance transport conduit extending from the proximal end to the distal end.

The invention also relates to a system for provisioning a device for personal care treatment with a substance to be dispensed from the device, said system comprising an instrument of the type mentioned in the opening paragraph.

The invention further relates to a container for cooperation with an instrument of the type mentioned in the opening paragraph and for provisioning a device for personal care treatment.

The invention finally relates to a device for personal care treatment having such a container.

Devices for personal care treatment that are adapted for dispensing substances for use in the treatment are known from the art, for instance in the form of electric shavers and toothbrushes. The substance to be dispensed is supplied from containers or reservoirs containing the substance. The container is to be mounted to the shaver, and via a passage the substance, for example a moisturizer, can be fed from the container to an outlet near the shaving head and distributed over the skin. The container is a replaceable container. Such a container holds enough substance for several shavings, and when it is empty it is discarded and replaced with a full one. Some known containers are largely made of a flexible material. The flexible material of the container makes it possible to force the substance out of the container by compressing the container.

In U.S. Pat. No. 6,220,772, an electric toothbrush comprising a container and a filling station for refilling the container is disclosed. The container contains toothpaste and communicates via a passage with an outlet situated in the brush. A pump is provided for feeding the toothpaste through the passage. The container in the toothbrush holds enough toothpaste for one brushing treatment. When the container is empty it can be refilled in the filling station via an inlet or filling opening.

The filling station has a cradle, a reservoir, a plunger system and a filling needle. The toothbrush can be inserted into the cradle of the filling station for refilling the container. By inserting the toothbrush into the cradle, the filling needle is inserted into the filling opening. The movement of the toothbrush into the cradle also activates the plunger system which forces the toothpaste via the filling needle into the container. The container is filled and the toothbrush can be removed from the cradle again for use.

In U.S. Pat. No. 6,039,301, a container is shown in which an opening for refilling the container is provided. The opening is sealable by a valve body. For filling the container, a filling needle is inserted into the opening and displaces the valve from a position closing off the passage to a position leaving the passage open. When the filling needle is retracted, the valve body is entrained back to its position closing off the passage.

A problem of these known systems is that the substance to be refilled is easily spilled, which is a waste and also often causes soiling of the system, clothing of the users and other items in the neighborhood of the system.

It is an object of the invention to allow refilling of the container with less risk of spilling and soiling.

According to the present invention, this object is achieved by providing an instrument according to claim 1. The invention may also be embodied in a system according to claim 9 including an instrument according to the invention, and also in a container according to claim 14, which is specifically adapted for use as part of a particular embodiment of the system according to the invention, and in a device for personal care treatment according to claim 20 including such a container.

In the instrument according to the invention, the sleeve immediately closes off the outlets of the filling needle when the filling needle is retracted from the filling passage present in the container. As a result, the risk of spilling and the associated likelihood of soiling are substantially reduced.

Particular embodiments of the invention are set forth in the dependent claims.

Further aspects, effects and details of the invention are set forth in the detailed description with reference to examples, of which some are shown in the drawings.

Below, an example of a system according to the invention for provisioning a device for personal care treatment with a substance to be dispensed from that device is described.

Figure 1:
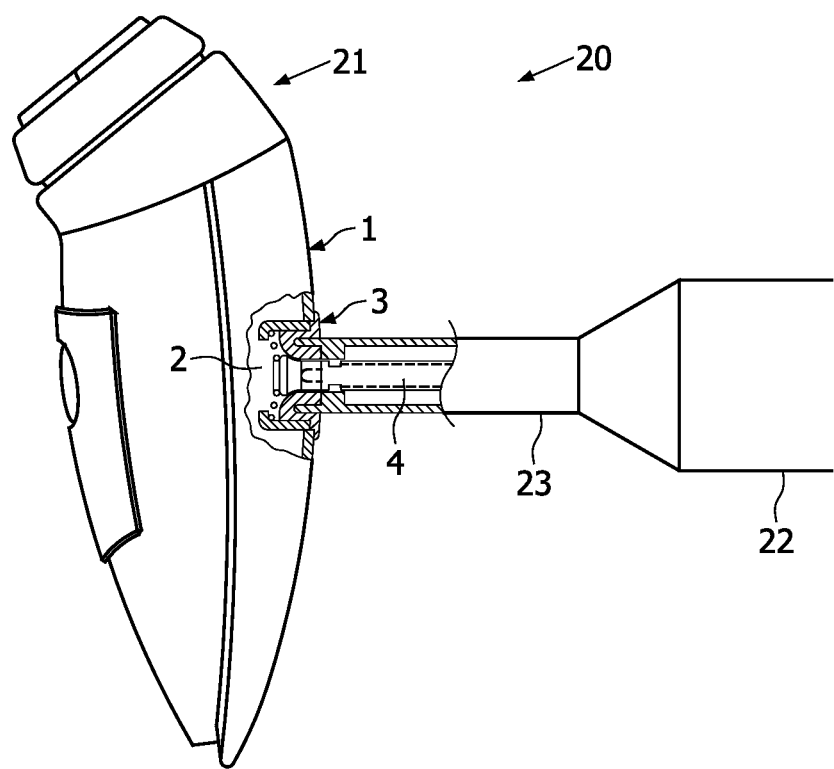
FIG. 1 is a side view of an example of a system according to the invention in combination with a shaver.

In FIG. 1, the system is generally designated by reference numeral 20. The system 20 according to the present example is composed of an instrument 23 in accordance with the invention, a storage reservoir 22 and a container 1. In FIG. 1, the instrument 23 is positioned against a refill socket 3 of the container 1 of a device 21 for personal care treatment, in particular a shaver. The refill socket 3 and parts of the container 1 and the filling instrument 23 are drawn in cross section. Although in the present example, the device for personal care treatment is a shaver with a moisturizer dispenser, it may also be a device for other kinds of treatment, such as for instance a toothbrush with a toothpaste dispenser, a massage device with a massage oil dispenser or a device for electric muscle stimulation with a dispenser for electrically conductive gel.

Figure 2:
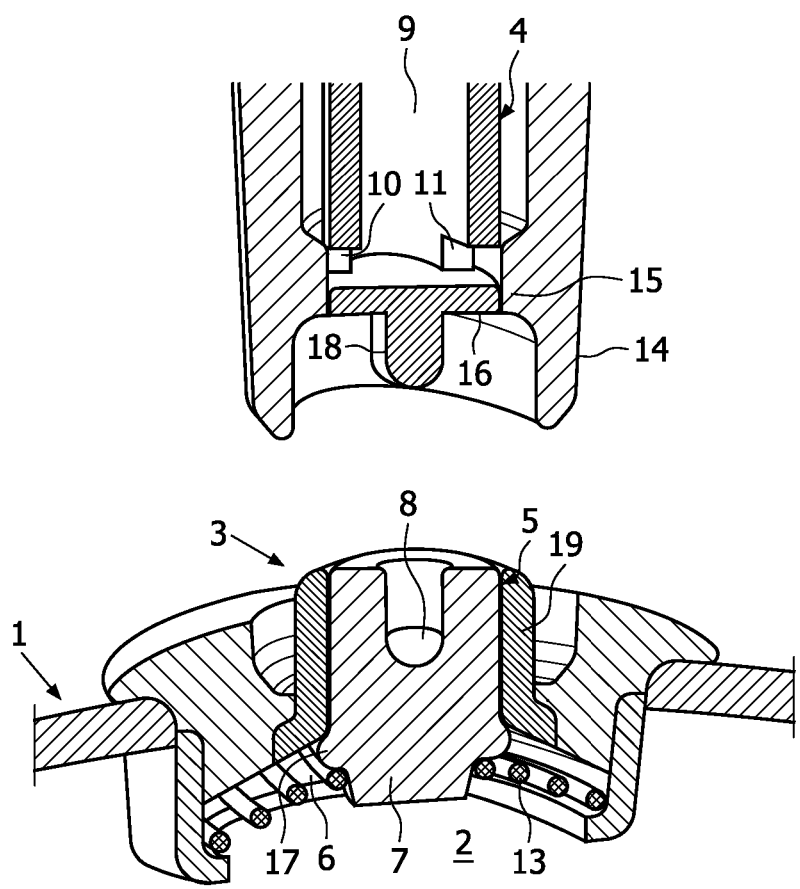
FIGS. 2-4 are cut-away perspective views of a refill socket and a filling needle of the system shown in FIG. 1, in a first position, a second position, and a third position.
Figure 3:
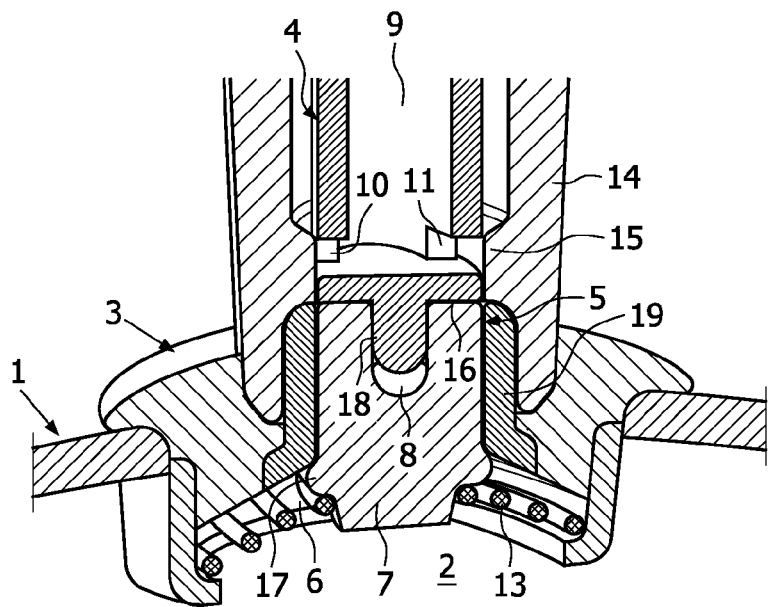
Figure 4:
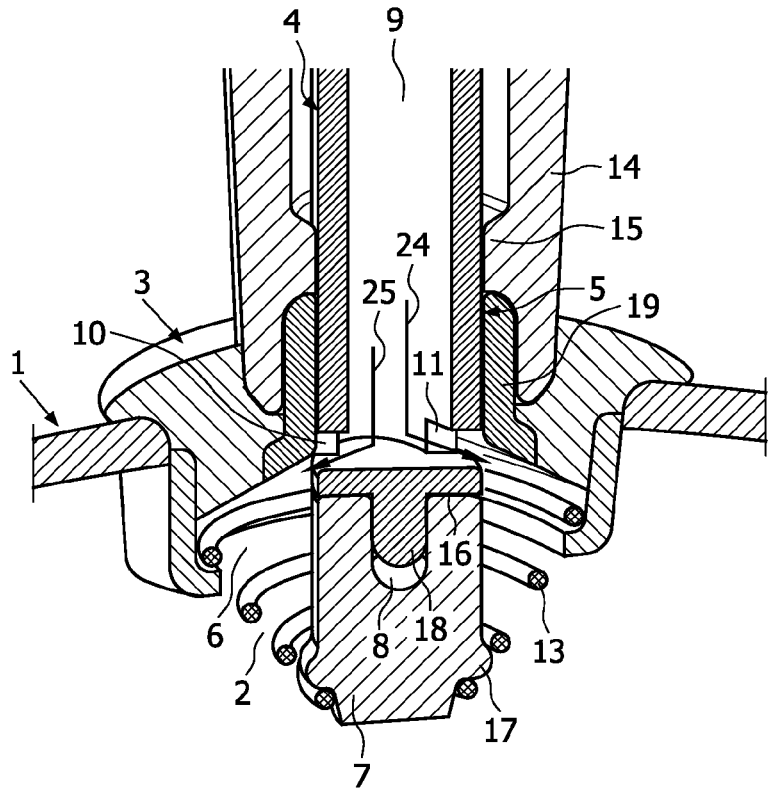

FIGS. 2-4 show successive steps of inserting a filling needle 4 of the instrument 23 into the refill socket 3. FIG. 2 shows the filling needle 4 and the refill socket 3 before making contact with each other. In FIG. 3, the filling needle 4 is positioned against a valve body 7, in the present example in the form of a plug, of the refill socket 3. In FIG. 3, the position of the filling needle 4 corresponds with the position of the filling needle 4 in FIG. 1. FIG. 4. shows the filling needle 4 in the filling position. In the present example, the cross-section of the filling needle 4 has a circular outer contour. However, for instance depending on preferences and the intended substance to be provisioned, the filling needle 4 may have a much larger (for instance finger-thick) or much smaller cross section, and the cross-section does not need to have a circular outer contour. Instead, the cross section may for instance also be oval, egg-shaped, trigonal or polygonal, and with rounded or sharp corners and with straight, hollow or outwardly bulged sides. Furthermore, the filling needle 4 is preferably straight, but may also be curved.

The filling needle 4 is provided with a sleeve with a guiding portion 14 and a closing portion 15. A proximal end of the filling needle 4 is connected to the storage reservoir 22, the size of which is preferably suitable for containing an amount of substance that is a multiple of the substance storage capacity of the container 1. A substance transport conduit 9 extends through the filling needle 4 from the proximal end to outlets 10, 11 provided in a radially facing surface portion closely adjacent a distal end of the filling needle 4. According to the present example, the filling needle 4 has a fully closed frontal face 16 at its distal end, which is useful for avoiding that substance is left on the valve body 7 after the filling needle 4 has been retracted. However, it is also possible to provide that the frontal face of the filling needle 4 is fully or partially open and that the outlets 10, 11 in the radially facing surface portion of the distal end of the filling needle 4 are instead provided, for example, in the form of axial recesses in a distal end rim of the needle wall.

The container 1 of the device 21 bounds a storage area 2 for storing a substance. The container 1 is removably connected to a substance dispensing structure (not shown) of the device 21. A passage 5 in the refill socket 3 extends from an inlet end outside the storage area 2 to a free space 6. The free space 6 constitutes a portion of the storage area 2. Alternatively, the free space 6 may also communicate with the storage area 2 of the container 1.

The passage 5 in the refill socket 3 has a narrowest section. In the present example, this narrowest section extends along the entire passage 5, but it may also constitute only a portion of the passage 5. The narrowest section has a cross-section providing a sealing fit with the distal end of the filling needle 4 when the distal end of the filling needle 4 extends therein. When the filling needle 4 is in a filling position, as is shown in FIG. 4, it extends past the narrowest section into the free space 6. The free space 6 extends radially from a continuation of the narrowest section of the passage 5 for receiving a filling substance that flows radially out of the outlets 10, 11 of the filling needle 4, when in the filling position. This flow of substance is depicted with arrows 24, 25 in FIG. 4.

In FIGS. 1-3, the valve body 7 is shown in a closed position, wherein a flange 17 of the valve body 7 seals off the passage 5 from the storage area 2 as it is pressed against an inner end of the passage 5. In FIG. 4, the valve body 7 is shown in an opened position spaced from the passage 5. The valve body 7 is held in its closed position by a spring 13. The valve body 7 can be moved from its closed position to its opened position by the distal end of the filling needle 4 exerting a force on the valve body 7 opposing the force of the spring 13.

The valve body 7 is suspended in a particularly simple and compact manner, because the spring 13 is spirally wound and comprises windings extending around the valve body 7 at least when the valve body 7 is in its open position.

While in the filling position, the filling needle 4 projects into the storage area 2 and extends through the narrowest section of the passage 5, the filling needle 4 contacting the valve body 7. When the filling needle 4 is retracted from the passage 5, the valve body 7 again closes off the passage 5. Alternatively or additionally, the seal between the valve body 7 and the passage 5 may also be located inside the narrowest section of the passage 5.

As can be seen in FIGS. 2 and 3, the valve body 7 in the closed position extends to the inlet end of the passage 5 when the filling needle 4 is retracted from the passage 5. Thus, the valve body 7 substantially fills up the passage 5 up to the inlet end, when it is in the closed position, so that no or very small amounts of substance residues in contact with the outside atmosphere can be left back in the passage 5 when the valve body 7 closes, and any substance left on an outwardly facing end of the valve body 7 can easily be wiped off. Moreover, the portion of the valve body 7 in the passage 5 does not occupy any part of the storage area 2, which is helpful for efficient use of the space available for the storage area 2.

For provisioning the container 1 with substance from the storage reservoir 22, the outlets 10, 11 of the filling needle 4 can be brought in communication with the storage area 2 by simply inserting the filling needle 4 into the refill socket 3. FIGS. 2-4 show successive steps of inserting the filling needle 4 into the refill socket 3.

By inserting the filling needle 4, the distal end of the filling needle 4 moves the valve body 7 from its closed position, sealing off the passage 5, into its opened position inwardly spaced from the narrowest section of the passage 5.

FIG. 4 shows the filling needle 4 in its filling position. Via the transport conduit 9 of the filling needle 4 and the radial outlets 10, 11 near the distal end of the filling needle 4, a substance can be fed into the storage area 2 of the container 1. In FIG. 4, arrows 24, 25 indicate the substance flow. The substance can be driven through the transport conduit 9, for example, by creating a pressure in the storage reservoir 22, by gravity, using a plunger, etc.

Because the narrowest section of the passage 5 has a cross-section providing a sealing fit with the distal end of the filling needle 4 when the distal end of the needle 4 extends therein in the filling position, the sides of the distal end of the filling needle 4 pass closely along the sides of this narrowest section of the passage 5 when the filling needle 4 is moved in or out of the refill socket 3. Thus, when the filling needle 4 is retracted out of the refill socket 3, the narrowest section scrapes off any substance present on the sides of the distal end of the filling needle 4. At the same time, this prevents any substance from passing out of the storage area 2 into the passage 5 prior to and during retraction of the filling needle 4. For counteracting that substance is left on the outside of the refill socket 3, it is advantageous that the valve body 7 extends to the inlet end of the passage 5, because the frontal face 16 of the filling needle 4 and the outside face of the valve body 7 are in contact from the moment the filling needle 4 enters the passage 5 up to the moment the filling needle 4 is free from the passage 5.

The distal end of the filling needle 4 has a frontal face 16 having a projection 18, and the valve body 7 has a recess 8 for releasable engagement with the projection 18. Because the projection 18 of the filling needle 4 and the recess 8 of the valve body 7 engage, the filling needle 4 is easily guided into a position coaxial with the passage 5 before entering into the passage 5, even though the valve body 7 in its closed position extends to the outer end of the passage 5, so that the filling needle 4 cannot be inserted into an outer portion of the passage 5 before engaging the valve body 7. As can be seen in FIG. 4, the co-operating projection 18 and recess 8 moreover keep the valve body 7 aligned with the filling needle 4 while the filling needle 4 is in the filling position and extends into the free space 6, and they ensure that the valve body 7 reliably returns to its position in the passage 5, closing off the passage 5 when the filling needle 4 is retracted from its filling position. The aligning effects can also be achieved if there is no sleeve around the filling needle, but they are helpful for aligning the filling needle and the sleeve with the passage.

When the container 1 has been filled, the filling needle 4 is retracted from its filling position and out of the refill socket 3. By retracting the filling needle 4, its sides, including the outlets 10, 11, are moved closely along the narrowest section of the passage 5. Because the narrowest section of the passage 5 has a cross-section providing a sealing fit with the distal end of the filling needle 4, any substance sticking to the sides of the filling needle 4 is scraped off by moving the filling needle 4 through the narrowest section of the passage 5.

Further, because the valve body 7 is forced towards its closed position by a spring 13, the frontal face 16 of the filling needle 4 is kept in contact with the contact surface of the valve body 7 while the filling needle 4 extends into the storage area 2 of the container 1. This part of the filling needle 4 as well as the outer surface of the valve body 7 therefore shield each other from contact with the substance, and will emerge from the refill socket 3, after filling the container 1, without any, or at least any substantial, amounts of the substance sticking to the filling needle 4 or to the outside of the valve body 7.

The frontal face 16 of the filling needle 4 is flat and axially facing, the projection 18 extends from the frontal face 16, and the outlets 10, 11 are located directly adjacent the frontal face 16. Due to these features, the filling needle 4 is easily guided into a coaxial position with the valve body 7 and the passage 5 before being inserted into the passage 5, while the filling needle 4 only needs to be inserted over a relatively short distance and the valve body 7 only needs to be displaced over a short distance and accordingly occupies relatively little space inside the container 1 when in the opened condition. This, in turn, is advantageous for the compactness of the container 1 at a given capacity. Such an effect may also be achieved with a hollow frontal face on the filling needle and/or with a recess in the filling needle instead of in the valve body and with a projection as part of the valve body instead of as part of the filling needle.

In the present example of the invention, the narrowest section of the passage 5 is bounded by a wall 19 made of a material that is softer than the material surrounding the wall. In the present example, the wall 19 is made of an elastomeric material, and the passage 5 has a cross-section slightly smaller than the outer cross-section of the filling needle 4. In this way, a sealing fit with the distal end of the filling needle 4 is possible without extremely tight manufacturing tolerances. The passage 5 bounded by the wall 19 made of the elastomeric material is also less prone to slanting of the filling needle 4 when the filling needle 4 is moving through the passage 5. Thus, the filling needle 4 is optimally guided. In a further embodiment, the narrowest section of the passage 5 is bounded by a ring of a material that is softer than the material bounding another section of the passage 5. Preferably, the narrowest section of the passage 5 is dimensioned to have a slightly smaller cross-section than the filling needle 4, so that the wall 19 is slightly stretched when the filling needle 4 is inserted and fits around the filling needle 4 with some pretension.

The closing portion 15 of the sleeve around the filling needle 4 is movable between a first position closing off the outlets 10, 11 and a second position proximally away from the first position and the outlets 10, 11, and is biased by a further spring (not shown) to its first position. In its first position, the closing portion 15 of the sleeve closes off the outlets 10, 11, so that substances are prevented from leaking out of the outlets 10, 11 when the filling needle 4 is not in the filling position.

When the filling needle 4 is moved into the refill socket 3, the closing portion 15 of the sleeve sealingly contacts a wall section of the passage 5, thereby bounding the narrowest section of the passage 5. Said wall section of the passage 5 prevents the sleeve from moving along with the filling needle 4 into the refill socket 3. As a result, when the filling needle 4 is moved further into the refill socket 3, the sleeve will be moved from its first position shown in FIG. 3 to its second position shown in FIG. 4 against the pretension force of said further spring (not shown), so that the outlets 10, 11 are released and moved out of the sleeve into the narrowest section of the passage 5 and further into the free space 6.

When the filling needle 4 is retracted from the refill socket 3 after filling, the further spring (not shown) will force the closing portion 15 of the sleeve back into its first position covering the outlets 10, 11 as the outlets leave the narrowest section of the passage 5. Thus, during retraction of the filling needle 4 from the refill socket 3, the outlets 10, 11 of the filling needle 4 are successively covered by the narrowest section of the passage 5 and by the closing portion 15 of the sleeve, so that leakage of the substance via the outlets 10, 11 is effectively counteracted not only during insertion of the filling needle 4 into the refill socket 3 but also during retraction of the filling needle 4 from the refill socket 3.

The sleeve of the filling needle 4 is provided with a guiding portion 14 for further guiding the filling needle 4 to an entry position coaxial with the passage 5. The guiding portion 14 has the form of a widened sleeve moveable along the filling needle 4, and is biased by way of the spring (not shown) to a position towards the distal end of the filling needle 4. In use, the guiding portion 14 of the sleeve makes contact with part of the refill socket 3 before the filling needle 4 contacts the refill socket 3. As shown in FIGS. 2-3, the guiding portion of the sleeve, and thus the filling needle 4, are initially positioned coaxially with the passage 5 before the filling needle 4 touches the valve body 7. To further facilitate the positioning, the guiding portion 14 of the sleeve and/or the protruding part of the passage 5 are beveled. Thus, the filling needle 4 can easily be positioned in line with the passage 5, and damage to the distal end of the filling needle 4 can be prevented. The guiding effect of the co-operating guiding portion 14 and the outwardly protruding portion of the wall 19 may be advantageous in addition to the guidance provided by the co-operating projection 18 of the filling needle 4 and recess 8 of the valve body 7.

The guiding portion 14 is also equipped to closely fit around a portion of the wall 19 bounding the narrowest section of the passage 5. When engaging the wall 19, the guiding portion 14 thus partially supports the narrowest section of the passage 5, thereby ensuring a tight fit around the distal end of the filling needle 4.

The closing portion 15 of the sleeve and the guiding portion 14 of the sleeve are integrated with each other and a single spring urges both the closing portion 15 and the guiding portion 14 of the sleeve into the distal position thereof.

Figure 5:
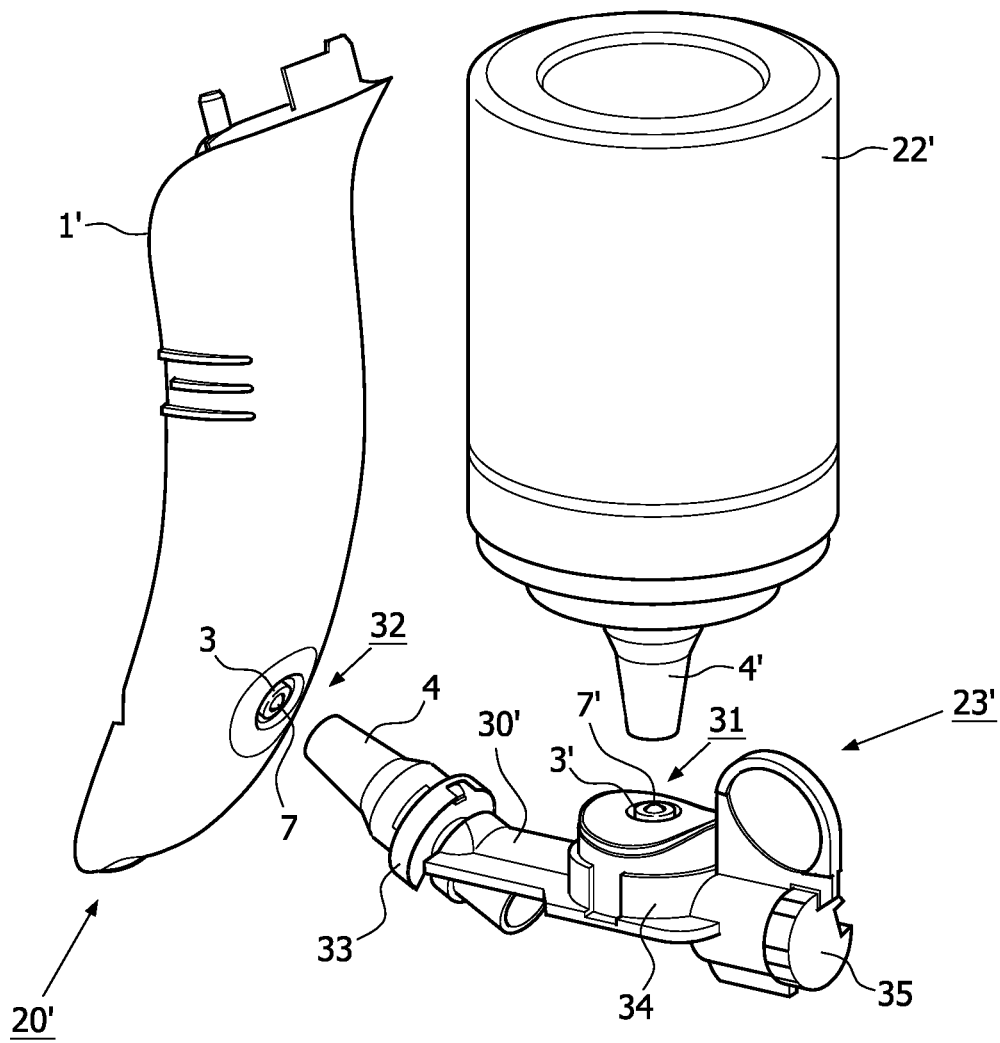
FIG. 5 schematically shows a number of parts of an alternative system according to the invention.

FIG. 5 schematically shows a number of parts of an alternative system 20' according to the invention. It is noted that FIG. 5 only shows a container 1', that belongs to a shaver not further shown in detail in FIG. 5, a storage reservoir 22', and an alternative embodiment of an instrument 23' according to the invention separately from each other. The following description explains how these parts cooperate with each other in the system 20'.

The instrument 23' comprises a so-called transposer 30 via which the storage reservoir 22' can be connected to the container 1'. The transposer 30 is arranged in a charge and refill stand for the shaver. The charge and refill stand is not shown in further detail in FIG. 5, as it is of a kind known to the skilled person, and serves to simultaneously store and electrically charge the shaver and to refill the container 1' with a substance from the storage reservoir 22'. For this purpose, the charge and refill stand comprises a first holding member (not shown in FIG. 5) for holding the shaver and a second holding member (not shown in FIG. 5) for holding the storage reservoir 22'. The first and second holding members may be of any suitable type known to the skilled person, e.g. as known from customary charge and refill stands for devices for personal care treatment. In FIG. 5, the container 1', the transposer 30 of the instrument 23' and the storage reservoir 22' are shown as separate parts, but in the stored positions of the shaver and the storage reservoir 22' in the charge and refill stand the storage reservoir 22' is coupled to the transposer 30 via a first coupling device 31 and the transposer 30 is coupled to the container 1' via a second coupling device 32, so that a flow of the substance can take place from the storage reservoir 22' to the container 1' via a fluid channel provided in the transposer 30.

The second coupling device 32 comprises a filling needle 4 and a movable sleeve around the filling needle 4 of a kind as shown in FIGS. 2-4 and provided on a distal end 33 of the transposer 30. The second coupling device 32 further comprises a refill socket 3 closed by a valve body 7 of a kind as shown in FIGS. 2-4 and provided on the container 1'. The first coupling device 31 may be of any kind providing a releasable connection of a proximal end 34 of the transposer 30 to the storage reservoir 22'. In the embodiment of FIG. 5, however, the first coupling device 31 is of a similar kind as the second coupling device 32 and comprises a filling needle 4' and a movable sleeve around the filling needle 4' of a kind as shown in FIGS. 2-4 and provided on the storage reservoir 22', and further comprises a refill socket 3' closed by a valve body 7' of a kind as shown in FIGS. 2-4 and provided near the proximal end 34 of the transposer 30. This has the advantage that refilling of the container 1' can also take place by direct coupling of the storage reservoir 22' to the container 1', i.e. without making use of the charge and refill stand. However, if refilling of the container 1' is intended to take place only by making use of the charge and refill stand, the first coupling device 31 may be of a different type allowing a releasable connection of the storage reservoir 22' to the transposer 30. The transposer 30 also comprises a removable plug 35 near its proximal end 34. When the plug 35 is removed the transposer 30 can be internally cleaned.

The system 20' allows an automatic refilling process of the container 1' when the shaver carrying the container 1' is placed in the charge and refill stand. For this purpose, the storage reservoir 22' may for example be provided with an internal electrical pumping system and with electrical connections (not shown in FIG. 5) that are connected to cooperating electrical connections provided on the charge and refill stand when the storage reservoir 22' is arranged in the charge and refill stand. Alternatively, the charge and refill stand may be provided with any suitable type of pumping system. The system 20' further allows the arrangement of any kind of sensor for measuring a physical property of the substance present in the transposer 30, for example its pressure or temperature.

From the foregoing it will be clear to the skilled person that, within the framework of the invention as set forth in the claims, also many variations other than the examples described above are conceivable. For example, for positioning the distal end of the filling needle 4 with respect to the passage 5, the entry of the passage 5 may be provided with slanting sides.

The invention claimed is:

1. An instrument for filling, from a storage reservoir, a substance supply container of a device for personal care treatment, wherein the substance supply container comprises a refill socket and, a passage in the refill socket, and a valve body that closes off the passage, the passage having an inlet end, and the valve body having a recess, and wherein the instrument comprises:
a filling needle having a proximal end which is suitable for connection to the storage reservoir, and having a distal end having a frontal face, a substance transport conduit extending from the proximal end to at least one outlet provided in a surface portion of the filling needle facing in a radial direction of the filling needle closely adjacent the distal end of the filling needle; and
a sleeve around the filling needle movable between a first position, in which the sleeve closes off the at least one outlet, and a second position, in which the sleeve is moved away from the first position and the at least one outlet towards the proximal end;
wherein the sleeve has a distal end face arranged for sealingly contacting the inlet end of the passage in the refill socket, and
wherein the frontal face of the distal end of the filling needle has at least one projection extending in an axial direction of the filling needle for releasable engagement with the recess of the valve body that closes off the passage.

2. The instrument according to claim 1, further comprising a spring for urging the sleeve towards the first position.

3. The instrument according to claim 1, wherein the at least one outlet is located directly adjacent the frontal face.

4. The instrument according to claim 1, wherein the storage reservoir connected to the proximal end of the filling needle.

5. The instrument according to claim 1, further comprising a coupling device for releasably connecting the proximal end of the filling need to the storage reservoir.

6. The instrument according to claim 5, further comprising a first holding member for holding the device for personal care treatment and a second holding member for holding the storage reservoir.

7. A system or provisioning a device for personal care treatment with a substance to be dispensed from the device, said system comprising:
an instrument for filling, from a storage reservoir, a substance supply container of the device, wherein the substance supply container comprises a refill socket, a passage in the refill socket, and a valve body that closes off the passage, the passage having an inlet end, and the valve body having a recess, the instrument including:
a filling needle having a proximal end which is suitable for connection to the storage reservoir, and having a distal end having a frontal face, a substance transport conduit extending from the proximal end to at least one outlet provided in a surface portion of the filling needle facing in a radial direction of the filling needle closely adjacent the distal end of the filling needle; and
a sleeve around the filling needle movable between a first position, in which the sleeve closes of the at least one outlet, and a second position, in which the sleeve is moved away from the first position and the at least one outlet towards the proximal end;
wherein the sleeve has a distal end face arranged for sealingly contacting the inlet end of the age in the refill socket, and
wherein the frontal face of the distal end of the filling needle has at least one projection extending in an axial direction of the filling needle for releasable engagement with the recess of the valve body that closes off the passage; and
a container bounding a storage area for storing the substance, said container being connected or connectable to a substance dispensing structure of the device, and having the refill socket for connecting the container to the filling needle in a filling position for filling the container, said refill socket comprising:

the passage which extends from the inlet end outside the storage area to a free space in or communicating with the storage area, said passage having a narrowest section, said free space inside of the narrowest section extending radially from the narrowest section of the passage or from a continuation of the narrowest section of the passage, for receiving a substance flow out of the at least one outlet of the filling needle in the filling position, and the valve body which is displaceable between the first position and the second position, the valve body in the first position closing off the passage, and the valve body in the second position being inwardly spaced from the narrowest section of the passage and contacting the filling needle in the filling position extending through the passage and holding the valve body in the opened position, wherein the sleeve contacts the inlet end of the passage (5) when the filling needle is in a position projecting into the passage.

8. The system according to claim 1, wherein the sleeve sealingly contacts the inlet end of the passage when the filling needle is in a position projecting into the passage.

9. The system according to claim 7, wherein the narrowest section of said passage has a cross-section providing a sealing fit with a tip end of the filling needle when the tip end of the filling needle in the filling position extends in said passage.

10. The system (20) according to claim 7, wherein in the closed position, the valve body extends at least to the inlet end of the passage when the filling needle is retracted from the passage.

11. The system according to claim 7, wherein the recess is outside of the valve body in releasable engagement with the projection of the filling needle when the filling needle projects into the passage.

12. A container for cooperation with an instrument for filling, from a storage reservoir, a substance supply container of the device, wherein the substance supply container comprises a refill socket, a passage in the refill socket, and a valve body that closes off the passage, the passage having an inlet end, and the valve body having a recess, the instrument including:

filling needle having a proximal end which is suitable for connection to the storage reservoir, and having a distal end having a frontal face, a substance transport conduit extending from the proximal end to at least one outlet provided in a surface portion of the filling needle facing in a radial direction of the filling needle closely adjacent the distal end of the filling needle; and a sleeve around the filling needle moveable first position, in which the sleeve closes off the at least one outlet, and a second position, in which the sleeve is moved away from the first position and the at least one outlet towards the proximal end;

wherein the sleeve has distal end face arranged for sealingly contacting the inlet end of the passage in the refill socket, the refill socket being configured to connect the container to the filling needle of the instrument in a filling position for filling the container and wherein the frontal face of the distal end of the filling needle has at least one projection extending in an axial, direction of the filling needle for releasable engagement with the recess of the valve body that closes off the passage, wherein the container is configured to hold a supply of a substance to be dispensed from a device for personal care treatment, said container bounding a storage ret for storing the substance, said container being connected or connectable to a substance dispensing structure of the device for personal care treatment, said refill socket comprising:

the passage extending from an inlet end outside the storage area to a free space in or communicating with the storage area, said passage having a narrowest section, said free space inside of the narrowest section extending radially from the narrowest section of the passage or from a continuation of the narrowest section of the passage, for receiving a substance flow out of the at least one outlet of the filling needle when the filling needle extends into said free apace, and the valve body which is displaceable between the first position and the second position the valve body in the first position closing off the passage and in the second position being inwardly spaced from at least the narrowest section of the passage, the valve body being arranged for contacting the filling needle when the filling needle extends into said free space for holding the valve body in the opened position, wherein the narrowest section is bounded by a wall of material that is softer than a material of the valve body, and wherein the recess is on outside of the valve body for releasable engagement with the projection of the filling needle.

13. The container according to claim 12, wherein the softer material is an elastomer material.

14. The container according to claim 12, wherein the valve body in its closed position extends least to the inlet end of the passage.

15. The container according to claim 12, further comprising a spring contacting the valve body and provided for urging the valve body to the closed position.

* * * * *